United States Patent
Dimpfel

[19]

[11] Patent Number: 6,157,857
[45] Date of Patent: Dec. 5, 2000

[54] APPARATUS FOR DETERMINING SLEEP STAGING

[76] Inventor: Wilfried Dimpfel, Am Pfad 8, D-35440 Linden, Germany

[21] Appl. No.: 09/203,617

[22] Filed: Dec. 1, 1998

[30] Foreign Application Priority Data

Jul. 24, 1998 [DE] Germany .......................... 198 33 497

[51] Int. Cl.[7] ........................................................ A61B 5/04
[52] U.S. Cl. ............................................................ 600/544
[58] Field of Search ............................... 600/544, 26, 545

[56] References Cited

U.S. PATENT DOCUMENTS

| | | | |
|---|---|---|---|
| 4,776,345 | 10/1988 | Cohen et al. ............................ | 600/544 |
| 4,869,264 | 9/1989 | Silberstein ............................... | 600/544 |
| 5,010,891 | 4/1991 | Chamoun ................................. | 600/544 |
| 5,047,930 | 9/1991 | Martens et al. ......................... | 600/544 |
| 5,154,180 | 10/1992 | Blanchet et al. ........................ | 600/544 |
| 5,299,118 | 3/1994 | Martens et al. ......................... | 600/544 |
| 5,320,109 | 6/1994 | Chamoun et al. ...................... | 600/544 |
| 5,356,368 | 10/1994 | Monroe ................................... | 600/544 |
| 5,406,957 | 4/1995 | Tansey .................................... | 600/544 |
| 5,601,090 | 2/1997 | Musha .................................... | 600/544 |
| 5,699,808 | 12/1997 | John ........................................ | 600/544 |
| 5,813,993 | 9/1998 | Kaplan et al. .......................... | 600/544 |

FOREIGN PATENT DOCUMENTS

WO 93/07804  4/1993  WIPO .

*Primary Examiner*—Cary O'Connor
*Assistant Examiner*—Navin Natnithithadha
*Attorney, Agent, or Firm*—Fitch, Even, Tabin & Flannery

[57] ABSTRACT

Small bandwidth frequency ranges are disclosed for frequency transformation and processing of EEG signals for determining sleeping staging with a sleep staging index ($S_F$) in which a frequency transformation of a time domain EEG signal from an EEG measuring device is supplied in a plurality of sub-band frequency ranges a, b, and c. Processing of the frequency domain transformed data is performed which ascertains values A, B, and C representative of the frequency range a from 4.75 to 6.75 Hz, the frequency range b from 12.75 to 18.5 Hz, and the frequency range c from 18.75 to 35.0 Hz or representative of least two of said frequency ranges and determines therefrom a sleep staging index $S_F$.

5 Claims, 2 Drawing Sheets

APPARATUS FOR DETERMINING SLEEP STAGING

BACKGROUND OF THE INVENTION

1. Field of the Invention

The present invention relates to an apparatus for determining sleep staging (the depth of sleep), particularly during anesthesia in a therapeutic/surgical operation.

2. Description of the Related Art

Sleep staging, both in physiological and in medicinally induced sleep, is usually determined visually by experienced experts who evaluate a patient's EEG and allocate values, which reproduce sleep staging, to individual periods of time lasting 20 to 30 seconds. Evaluation is based on work by Rechtschaffen & Kales from 1969 and is nowadays the only generally recognized standard for assessing and ascertaining human sleep staging on the basis of an EEG.

It is evident that this technique is unsuited to being performed on a fairly large scale or during a therapeutic/surgical operation for which the patient is put into a medically induced sleep (anesthesia). For this reason, numerous tests have been performed to determine sleep staging on the basis of the EEG signal. In particular, EEG signals were transformed (fast Fourier transformation) for this purpose and the representation of the EEG signal in the frequency range underwent evaluation. Particular attention was placed on frequencies which were generally designated as A waves and ranged from about 0 to 3.5 Hz. These EEG signal portions of a very long wavelength were associated with the state of consciousness known as "sleep" and methods were developed which were intended to enable determination of sleep staging on the basis of these frequencies. The results were verified by comparing the automatically determined sleep staging with the sleep staging visually determined by experts according to the recognized Rechtschaffen & Kales technique.

The methods so far used did not, however, produce any reliable results or produced results that could only be applied with considerable qualification, so that ultimately a reliable, fully automatic determination of sleep staging is not possible to this very day.

In addition to the aforementioned efforts to determine the state of consciousness known as "sleep" in a universally valid manner that can be automated, there were experiments to evaluate medically induced sleep in particular. To an extent individual frequency ranges were also examined beyond the A wave range. Moreover, success here was only moderate and was restricted to the particular drug being examined, so that it was impossible to apply the results to other drugs. The validation of the results by means of a visual assessment based on Rechtschaffen & Kales also proved deficient, thus making it hardly possible to speak of a reliable evaluation of human sleep.

Knowledge about sleep staging is not just of interest to scientific or medical studies and applications. The absence of medically induced sleep during a therapeutic/surgical operation represents discomfort for the patient which is scarcely conceivable for anyone not affected. This applies all the more so if in addition to the absence of medically induced sleep, the medically induced insensitivity to pain is not achieved either and if at the same time the paralyzation of muscular activities, which is regularly provided during anesthesia, is successfully induced. As far as patients are concerned, this ultimately means that a therapeutic/surgical operation is performed without their being asleep and insensitive to pain, but without their ability to draw attention to their condition. This situation can be remedied by a reliable identification of sleep which is performed fully automatically and which also runs its course during a therapeutic/surgical operation and the anesthesia entailed thereby.

SUMMARY OF THE INVENTION

Yet regardless of the aforementioned and usually rare case of anesthetic failure, there is fundamental interest in a reliable technique for the qualified and quantitative determination of the state of consciousness known as sleep, with the result that the object upon which the invention is based is to be regarded as designing an apparatus that can be used to determine sleep staging reliably and fully automatically on the basis of the EEG signal.

This object is solved by an apparatus comprising the features of claim 1. Advantageous embodiments are arrived at from the dependent claims.

The invention is based on the knowledge that it is necessary to use at least two of three characteristic ranges of the EEG signal depicted in the frequency range in order to determine a sleep staging index $S_F$. What is decisive is that the EEG signal is examined in relation to these ranges and the sleep staging index $S_F$ is ascertained by taking account of at least two ranges, though preferably all three ranges are considered.

BRIEF DESCRIPTION OF THE DRAWINGS

An exemplary embodiment of the apparatus according to the invention will now be described in more detail with reference to the Figures.

DETAILED DESCRIPTION OF THE PREFERRED EMBODIMENTS

Figure 1:
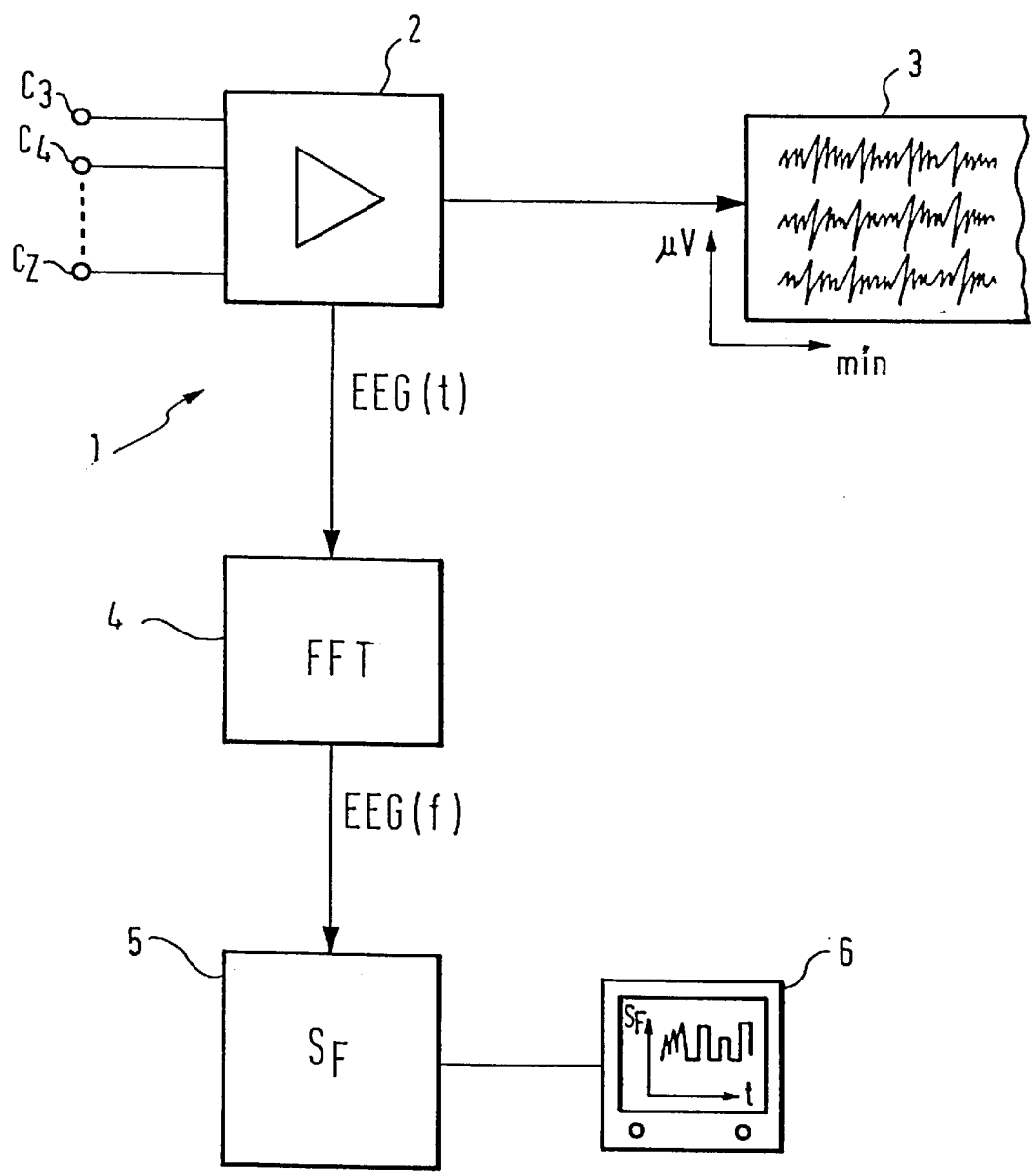
FIG. 1 schematically shows the structure of an exemplary embodiment of the apparatus according to the invention.

FIG. 1 schematically depicts an exemplary embodiment of the apparatus according to the invention. An exemplary embodiment comprises an EEG measuring device 1, of which just the electrodes $C_3$ and $C_4$ and the electrode $C_Z$ are shown in FIG. 1. A standard EEG measuring device normally comprises 15–25 electrodes in addition to the electrode $C_Z$. The output signals of the electrodes are supplied to an amplifier 2 which amplifies and processes the electrode signals in such a way that it is thereby possible to control a recorder (not depicted) which records the EEG 3. In the apparatus according to the invention, an EEG signal, preferably that of the electrodes $C_3$ and/or $C_4$, is diverted from the EEG measuring device 2 and supplied to transformation means 4 to perform a Fourier transformation (fast Fourier transformation, FFT). The connection between the EEG measuring device 2 and the transformation means 4 can be established in various ways, preferably via an optical connection, e.g. a glass fiber, thus reliably excluding interference with the transmitted EEG signal even in the case of longer transmission routes.

Figure 2:
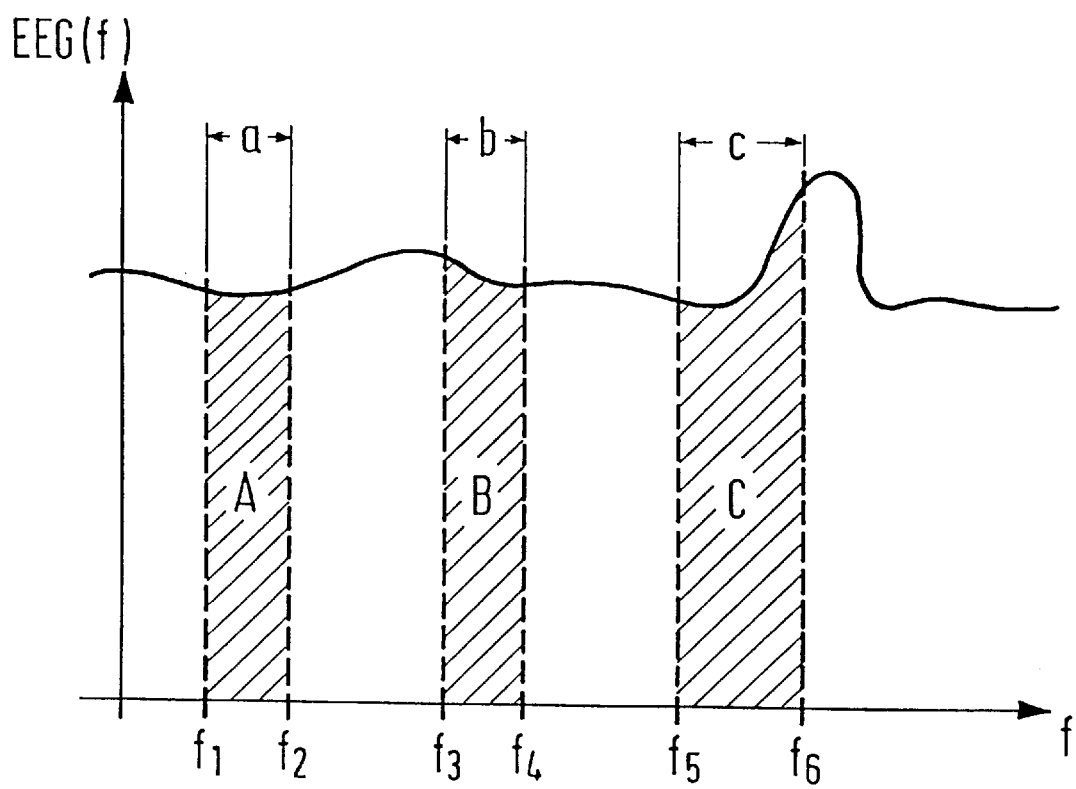
FIG. 2 schematically shows the course of the EEG signal in the frequency range and the ranges to be taken into consideration according to the invention.

The output signal from the transformation means 4 forwards the Fourier-transformed EEG signal to processing means 5 which further processes the EEG signal EEG(f) now present in the frequency range. For this purpose, three frequency ranges of the transformed EEG signal are more accurately examined. The frequency ranges are shown in FIG. 2, whereby the frequency range a extends from 4.75 to 6.75 Hz, the frequency range b extends from 12.75 to 18.5 Hz and the frequency range c extends from 18.75 to 35.0 Hz. The processing means 5 determines a representative value A, B and C for each of the frequency ranges and ascertains therefrom the index $$S_F = \frac{A+B}{C}$$

which characterizes sleep staging.

The sleep staging index $S_F$ reliably reflects the patient's sleep staging, as could be proved in a validation study with respect to the sleep conditions ascertained according to Rechtschaffen & Kales.

The values A, B and C representative of the three frequency ranges a, b and c can be obtained in various ways. What is decisive is that at least two of the frequency ranges a, b and c, though preferably all three, are completely or partly taken into consideration when determining the representative values. A method of determining representative values is to integrate the transformed EEG signal from the initial frequency until the final frequency of the respective range or of a section within the range.

The hatched areas in FIG. 2 reproduce the representative values A, B and C which are ascertained by the integration of the transformed EEG signal in the frequency ranges a, b and c. In principle, however, an average of the transformed EEG signal, which is determined via the individual frequency ranges a, b and c, is also suitable as a representative value.

As shown in FIG. 1, the exemplary embodiment of the apparatus according to the invention described here comprises a monitor 6 to represent the sleep staging index $S_F$. In addition to a representation on a monitor, the signal $S_F$ can also be used for other purposes, e.g. as an alarm. The $S_F$ signal can also be supplied to the EEG recorder (not shown) with the result that the sleep staging index SF is also reproduced on the EEG 3.

It should be noted that the apparatus according to the invention indicates an index which has so far not been determined in this form and which is designated as the sleep staging index $S_F$. This index differs from those values so far calculated and makes it possible to determine physiological and medically induced sleep, regardless of the medicine used.

The transformation means and the processing means are preferably combined within a personal computer which can also make available the computing speed necessary for transforming the EEG signal into the frequency range and/or for processing the transformed EEG signal, i.e. for determining the sleep staging index $S_F$.

What is claimed is:

1. An apparatus for determining sleep staging comprising:

a transformation means to which an output signal (EEG (t)) of an EEG measuring device is supplied and which transforms the supplied EEG signal into a frequency range comprising a plurality of sub-bands including frequency ranges a, b, and c; and a processing means to which the EEG signal (EEG(f)) transformed into the frequency range is supplied from said transformation means and which ascertains values A, B and C representative of the frequency range a from 4.75 to 6.75 Hz, the frequency range b from 12.75 to 18.5 Hz and the frequency range c from 18.75 to 35.0 Hz or representative of least two of said frequency ranges and determines therefrom a sleep staging index $S_F$.

2. An apparatus according to claim 1, wherein said processing means determines said sleep staging index SF as a quotient of the sum of said representative values A and B and said representative value C $$\left(S_F = \frac{A+B}{C}\right).$$

3. An apparatus according to claim 2, wherein said processing means ascertains said representative values A, B and C by integration of the EEG signal in the frequency range.

4. An apparatus according to claim 2, wherein said processing means ascertains said representative values A, B and C by averaging the EEG signal in the frequency range.

5. An apparatus according to claim 4, wherein said transformation means transforms the supplied EEg signal (EEG(t)) into the frequency range by means of a fast fourier transformation (FFT).

* * * * *